United States Patent
Ferrari

[11] Patent Number: 5,265,579
[45] Date of Patent: Nov. 30, 1993

[54] X-RAY TRANSPARENT MONITORING ELECTRODE AND METHOD FOR MAKING

[76] Inventor: R. Keith Ferrari, 6525 Radcliff Dr., Nashville, Tenn. 37221

[21] Appl. No.: 947,490

[22] Filed: Sep. 21, 1992

[51] Int. Cl.⁵ .......................................... A61B 5/0408
[52] U.S. Cl. ...................... 128/640; 29/825; 29/854
[58] Field of Search ............. 128/640, 639; 29/825, 29/854

[56] References Cited

U.S. PATENT DOCUMENTS

| | | |
|---|---|---|
| 3,888,240 | 6/1975 | Reinhold, Jr. . |
| 4,050,453 | 9/1977 | Castillo et al. ............... 128/640 |
| 4,102,331 | 7/1978 | Grayzel et al. ............... 128/640 |
| 4,257,424 | 3/1981 | Cartmell . |
| 4,685,467 | 8/1987 | Cartmell et al. . |
| 4,748,983 | 6/1988 | Shigeta et al. . |
| 4,911,169 | 3/1990 | Ferrari . |
| 5,082,595 | 1/1992 | Glackin . |

FOREIGN PATENT DOCUMENTS

49539  2/1989  Japan ...................... 128/639

Primary Examiner—Lee S. Cohen
Attorney, Agent, or Firm—Vernon J. Pillote

[57] ABSTRACT

A biomedical monitoring electrode assembly including an X-ray translucent multi-element back electrode assembly adapted to be adhesively attached to the body of a patient, and a reference electrode adapted for positioning remote from the back electrode, preferably on the limb of a patient. An X-ray translucent lead wire assembly is attached to the back electrode assembly with two of the leads connected to the two electrodes of the back electrode assembly and another lead extending from the back electrode assembly to the remote reference electrode.

27 Claims, 3 Drawing Sheets

X-RAY TRANSPARENT MONITORING ELECTRODE AND METHOD FOR MAKING

BACKGROUND OF THE INVENTION

In the care of infants, and particularly premature infants, it is frequently necessary to substantially continuously monitor their heart functions and many premature infants also require frequent X-rays of the upper chest area to evaluate lung conditions. However, premature infants usually have a very low birth weight and require very little radiation to generate an X-ray so that metal parts and even some non-metalic parts having significant mass which are located in the infant's chest area during the X-ray, will produce images on the X-ray film. Thus, if the electrodes or the lead wires or any connections between the electrode and the lead wires disposed within the chest area of the infant have metallic parts or even non-metallic parts of substantial mass, they should be removed each time an X-ray is taken and then replaced. Removing and replacing the electrodes is not only time consuming but also increases the likelihood of dermal irritation or ulceration to the very thin skin of an infant. Further, monitoring is interrupted whenever the electrodes are removed.

The patent literature discloses various electrode constructions described as being X-ray translucent. Some such as described in U.S. Pat. No. 4,257,424 use a thin layer of conductive paint on a thin flat elongated substrate to form both the electrode and an extended lead, and others such as disclosed in U.S. Pat. Nos. 3,888,240 and 4,748,983 form a sheet electrode and a lead strip from a conductive carbon filled plastic material. The leads in such electrode assemblies are in the form of thin and relatively wide uninsulated bands and present some problems in handling and insulating, particularly if the leads are made sufficiently long to extend outside of the patient's chest area. Some other electrode constructions such as disclosed in U.S. Pat. No. 4,685,467, use a button type electrode with a snap-on connector to connect the lead wire to the electrode. The button electrode with snap-on connector has a substantial mass which not only reduces the X-ray transparency of the electrode assembly, but also produces an uneven and relatively high profile electrode assembly which would be uncomfortable if positioned on the back of a patient. Electrodes have also been heretofore made in which sheathed carbon fiber conductor was connected to a carbon filled disk type electrode by sonic welding. However, sonic welding can only be used with relatively thick disk electrodes which are not X-ray transparent.

It is an object of the present invention to provide a biomedical monitoring electrode adapted to be adhesively affixed to the patient for continuous ECG monitoring, and in which the overall electrode assembly including the electrode member and electrical lead means and the connection between the electrode and the electrical lead means are X-ray transparent even at the relatively low level exposures used in infant X-rays, so that it is unnecessary to remove and replace electrodes in the chest area when taking X-rays.

A more particular object of this invention is to provide a biomedical monitoring electrode assembly including a multi-element back electrode adapted to be adhesively affixed to the back of an infant, and a reference electrode adapted for positioning remote from the back electrode and in which the back electrode including the leads and the connection between the electrodes and leads is X-ray transparent so that it is unnecessary to remove and replace the electrodes when taking chest X-rays.

SUMMARY OF THE INVENTION

One aspect of this invention is an X-ray transparent biomedical monitoring electrode comprising a flat X-ray transparent sheet electrode member of thin carbon filled polymer material having a layer of skin compatible conductive adhesive contacting a lower side of the electrode member; X-ray transparent lead means having a carbon fiber conductor and an insulating sheath, and X-ray transparent attaching means conductively attaching the carbon fiber conductor to the upper side of the electrode member. A cover member of electrically insulative material is adhesively attached to the upper side of the sheet electrode member and to the electrical lead means.

Another aspect of this invention is a monitoring electrode assembly including a multi-element back electrode means and a reference electrode means adapted for positioning remote from the back electrode means, preferably on a limb of the patient. The multi-element back electrode includes X-Ray transparent first and second sheet electrode members of thin carbon filled polymer, and an X-ray transparent web member of electrically insulative material having a first portion adhered to the lower face of the first electrode member and a second portion adhered to the lower face of the second electrode member, and a central portion intermediate the first and second electrode members, and first opening means in the first portion of the web member inwardly of the periphery of the first sheet electrode member and second opening means inwardly of the periphery of the second sheet electrode member. A first layer of skin compatible conductive adhesive on the lower face of the first portion of the web member directly contacts the first sheet electrode member at the first opening means and a second layer of skin compatible conductive adhesive on the lower face of the the second portion of the web member directly contacts the second electrode member at the second opening means in the web member. X-ray transparent first, second and third electrical lead means each having a carbon fiber conductor and a sheath of electrically insulative material, have an intermediate section adhesively anchored to the web member. The first lead means has the carbon fiber conductor at one end conductively attached to the upper face of the first electrode member and the second lead means has the carbon fiber conductor at one end conductively attached to the upper face of the second electrode member. The third lead means has a length substantially longer than the first and second lead means to extend a substantial distance from the back electrode and the end of the third lead means is conductively attached to the reference electrode. An X-ray transparent cover member of electrically insulative material overlies and is adhered to the upper faces of the first and second electrode members and to an intermediate section of the first, second and third lead means to aid in anchoring the lead means to the back electrode.

The back electrode assembly is adapted to be adhesively attached by the skin compatible conductive adhesive to the skin of an infant and the back electrode assembly including the electrode members, the lead wires and the connection between the lead wires and the electrode members are X-ray transparent, even at the low level exposures used in infant X-rays, so that it is not necessary to remove and replace the electrodes when taking X-rays and monitoring can continue during the X-rays. The back electrode assembly also has a thin flat profile so that it can remain comfortably affixed to the back of the infant for long periods. Further, the electrode construction is such that it can be easily and economically produced.

DETAILED DESCRIPTION OF THE INVENTION

Figure 1:
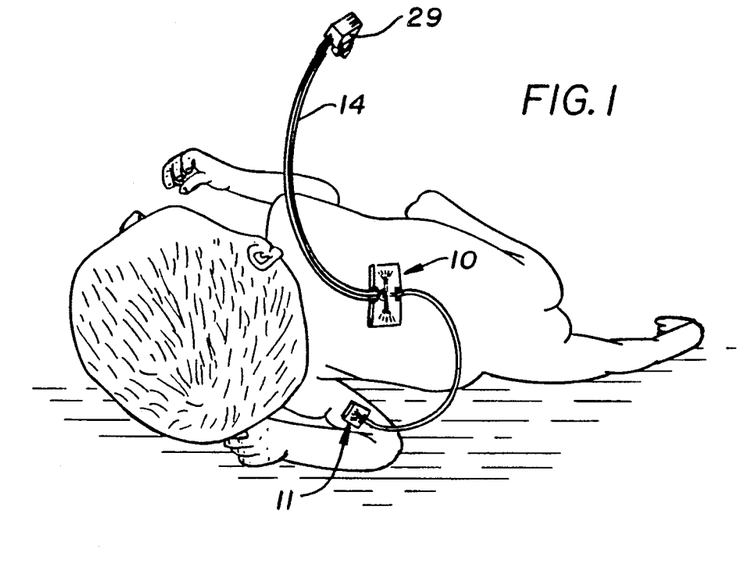
FIG. 1 is a perspective view illustrating attachment of the electrode assembly to the body of an infant.

In the preferred embodiment illustrated, the monitoring electrode assembly includes a multi-element back electrode 10 and a reference electrode 11 that is positioned remote from the back electrode, as illustrated in FIG. 1 of the drawings. In general, the multi-element back electrode 10 includes an X-ray translucent web member 15 of thin, flexible electrically insulative material; flat X-ray transparent first and second sheet electrode members 17 and 18; first and second layers or patches of skin compatible conductive adhesive 20 and 21; an X-ray transparent lead means 24, and an X-Ray transparent cover member 23 of electrically insulative material.

The X-ray transparent non-conductive web member 15 is formed from a thin sheet of flexible paper or plastic; for example, 3.5 mil polyethylene plastic, and is made sufficiently large to enable the first and second electrode members to be adhesively affixed to different portions or zones of the web member with the electrode members laterally spaced apart to electrically isolate the same from each other. More particularly, the first sheet electrode member 17 overlies a first portion of the web member and the second sheet electrode member 18 overlies a second portion of the web member, and the first and second sheet electrode members are separated from each other by an intermediate portion of the web. The web member 15 has a layer 16 (FIG. 4) of pressure sensitive adhesive, such as a pressure sensitive acrylic adhesive on the upper side thereof.

The X-ray translucent electrodes 17 and 18 are formed of a thin sheet of conductive carbon or graphite filled polymer film such as graphite filled polyvinyl chloride or polycarbonate polymer film. The film is very thin, preferably of the order of 1 to 4 mils thickness, to reduce the overall mass of the electrodes. An example of carbon filled polymer which can be used is thin carbon black filled polycarbonate film available from Mobay Corporation under the trademark "Macrofol" product KL3-1009. It is also contemplated that a fine mesh screen formed of carbon filled polymer fibers such as PVC or polyester polymers could be used. In order to provide for rapid defibrillator recovery, the electrodes 17 and 18 have a thin coating 17a, 18a (FIG. 5) of silver/silver chloride (AG+/AG+CL−) on one face, preferably the lower face. The thin silver/silver chloride coating is of the order is of a few microns in thickness, for example four to six microns, and is applied to graphite filled polymer used to make the electrodes by silk screening or by flexographic printing or by vapor deposition over the full web width and such thin layers of silver/silver chloride do not impair the X-ray transparency of the carbon filled sheet electrode members.

The sheet electrode members 17 and 18 are adhesively attached at the first and second electrode zones of the web member by the pressure sensitive adhesive layer 16 on the web member. The web member has openings 15a and 15b respectively extending therethrough and located inwardly of the periphery of the respective sheet electrode members. The skin compatible conductive adhesive layers 21 and 22 are used to adhere the electrodes to the skin of the patient and to detect biomedically generated electrical signals. The adhesive layers are preferably a skin compatible ionically conductive pressure sensitive solid gel adhesive, and may for example, be a conductive adhesive marketed by Medtronic, Inc. under the trademark "Promeon" No. RG63b. The conductive adhesive layers 21 and 22 underlie and adhere to the web member around the openings 15a and 15b and the layers 21 and 22 of conductive adhesive respectively contact the lower face of the electrode members 17 and 18 through the openings 15a and 15b in the web member. As will be seen, adjacent edges of the electrode members 17 and 18 are spaced apart a preselected distance to electrically isolate the electrode members from each other and the openings 15a and 15b are spaced apart a substantially greater distance than the spacing between adjacent edges of the electrode members. The openings 15a and 15b define the area in which each electrode member contacts the associated layer of conductive adhesive and define the effective area of the electrode members. Thus, the effective areas of electrode members 17 and 18 defined by openings 15a and 15b are spaced apart a distance substantially greater than the spacing between the electrode members. A release sheet 28 such as a sheet of polyester with a release coating of silicone or the like on one side, underlies the layers 20 and 21 of conductive adhesive and provides a backing against which the components of the electrode members can be trimmed during production of the electrode assembly and also functions as a holding card for the electrode assembly until it is ready for use.

The X-ray translucent leads 24 are of a type having a tow of carbon fibers comprising from about 1000 to 3000 fibers insulated by an X-ray transparent plastic sheath such as polyurethane. At least one conductive lead is provided for each electrode and, although separate leads could be used, it is preferable to use a multi-conductor cable such as a flat multi-conductor cable having at least one conductor for each electrode.

The leads are arranged to extend from the back electrode at least to a location outside the chest area of the patient to which the back electrode is attached, to avoid the necessity of further lead connectors within the chest area when it is X-rayed. The leads can be made long enough to extend to a remotely positioned monitoring instrument. However, the electrodes generally would not be reused for different patients, and in order to minimize cost of the disposable electrode assembly, it is preferred that the leads only have a length to extend from the back electrode 10 a distance sufficient to enable connection to a junction box or cable extension located outside of the chest area. In the embodiment illustrated, a multi-terminal connector 29 is mounted on the distal end of the multi-conductor lead for connection to a junction box or cable extension. The connector may, for example be the same as or similar to an RJ11 telephone connector.

A sheathed intermediate section of the multi-conductor cable overlies the web member 15 at the zone intermediate the electrode members 17 and 18 and is attached by the adhesive coating 16 to the web member 15. A first lead 24a has an end conductively attached by X-ray transparent means 31 to the electrode member 17 and a second lead 24b has an end conductively attached by X-ray transparent means 31 to the electrode 18. Carbon fiber conductors generally exhibit anisotropic conductivity, with good conductivity in the direction of the length of the fibers and very low conductivity in a direction crosswise of the length of the fibers. This anisotropic characteristic of the carbon fiber leads aggravates the problem of making an X-ray transparent connection between the leads of the sheet carbon filled polymer electrodes. As previously discussed, sonic welding techniques have been used to connect carbon fiber conductors to disk type electrodes and in effect fuse the carbon filaments with the disk. However, sonic welding is not suitable for connecting carbon fiber leads to thin sheet electrodes and the use of disks sufficiently thick to allow sonic welding, adversely affects the X-ray transparency of the completed electrode. Conductive epoxy adhesive such as carbon impregnated epoxy adhesive have also been used, but such adhesives not only significantly increase the mass of the connection between the carbon fiber conductors and the electrode and reduce the X-ray transparency, but also complicates and slows down the production of the electrodes.

Applicant has found that the carbon fibers on the stripped ends of the leads can be conductively attached to the electrodes using non-conductive pressure sensitive tape if the fiber conductors are coated with an electrically conductive coating. The fibers may be coated by dipping the ends of the fiber conductors in a conductive ink or by applying a drop of conductive ink on the fibers or on the electrode during mounting of the fiber conductor on the electrode with a piece of non-conductive pressure sensitive tape. The conductive ink may, for example, comprise a conductive silver/silver chloride ink or a conductive carbon ink or a carbon and silver/silver chloride ink. Some examples of suitable inks are conductive inks marketed by Ercon Incorporated under the tradenames Ercon E-1700, a silver ink; Ercon E422, a carbon-silver ink and Ercon N-361, a carbon ink with the carbon ink being preferred for X-ray transparency. It is also contemplated that the carbon fibers could be coated during manufacture of the conductors with a metallic coating such as nickel that is sufficiently thin for example a 5 or 6 microns in thickness and such as to not impair the X-ray translucency of the wire and which would enhance conduction between the carbon fibers and the carbon electrode members. The use of conductive inks introduces some problems in production and the use of metal coated carbon fiber leads substantially increases the cost of the carbon fiber leads.

It has also been found that the carbon fiber leads can be conductively attached to the carbon film electrodes without requiring use of conductive ink or a metal coating on the carbon fibers by use of double sided pressure sensitive tape of a type having electrical conductivity along the X, Y and Z axes. More particularly, electrically conductive pressure sensitive tape having good conductivity only in a direction transverse to the thickness of the film did not produce a connection between carbon fibers of the lead and the carbon electrodes having sufficiently low impedance to meet the AAMI standards for disposable ECG electrodes for AC impedance and defibrillation overload recovery. However, conductive double face pressure sensitive tape of a type having a non-woven open mesh conductive carrier matte with conductive pressure sensitive adhesive on both sides of the matte and providing conductivity in the X, Y and Z axes, viz. conductivity both in the plane of the tape and transverse to the plane of the tape, did produce a connection between the anisotropically conductive carbon fibers of the leads and the carbon filled polymer film electrode which met all of the AAMI standards for disposable ECG electrodes. The conductive carrier matte is a thin non-woven open web of less than five mills in thickness, comprised of semi-metallic fibers such as carbon fibers or non-metallic fibers such as polyester fibers and in which the fibers are metal plated or coated before or after being formed into a web. The non-metallic and semi-metallic fibers are X-ray transparent before plating or coating and the metal plating or coating of the fibers of the web is made sufficiently thin, for example less than ten microns in thickness, and such that the thin open-mesh web formed of the metal plated fibers remains X-ray transparent. The conductive pressure sensitive adhesive may comprise various pressure sensitive adhesives loaded with sufficient carbon or graphite for electrical conductivity. An example of the conductive double face pressure sensitive tape with a conductive carrier which can be used is a thin pressure sensitive bonding tape available from Adhesives Research, Inc., Glen Rock, Pa. under the trademark "Arclad", product No. 8001. This tape comprises a non-woven open mesh matte or carrier formed of metal coated carbon filaments having a metal coating of a few microns, for example five or six microns in thickness, and such that the metal coated matte is X-ray transparent. The electrically conductive pressure sensitive adhesive comprises a pressure sensitive adhesive impregnated with carbon or graphite for conductivity. U.S. Pat. No. 5,082,595 assigned to Adhesive Research, Inc. discloses a method of making such a double faced pressure sensitive adhesive tape with conductivity in X, Y and Z axes.

Figure 4:
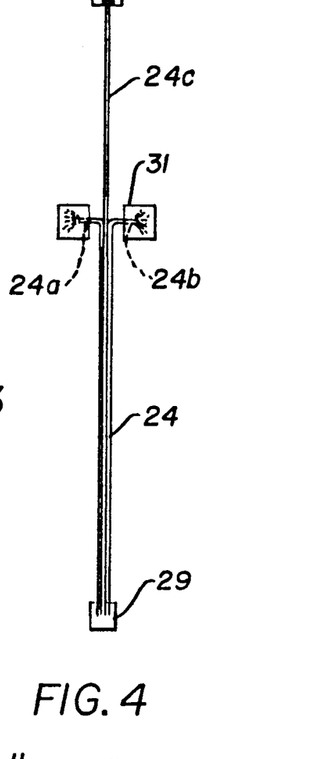
FIG. 4 is a plan view of a lead wire sub-assembly.
Figures 8, 9:
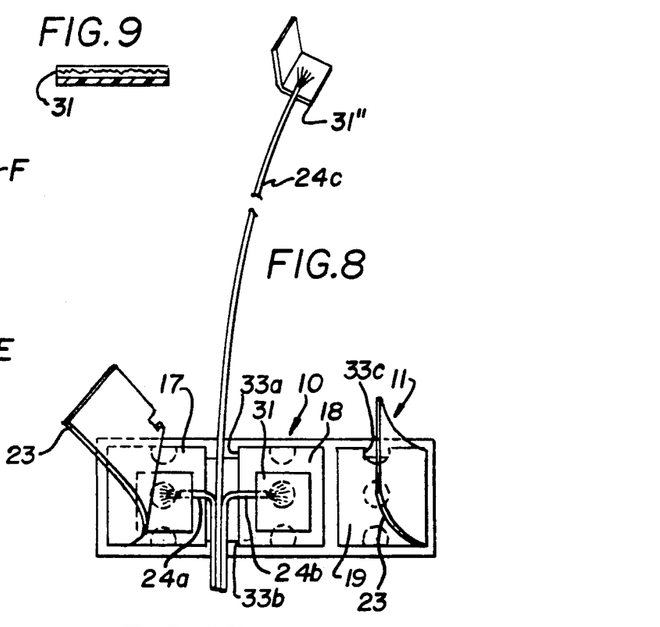
FIG. 8 is a view illustrating assembly of the electrical leads on the electrodes.
FIG. 9 is a sectional view through a piece of conductive tape for conductively attaching the carbon fiber leads to the electrodes.

A third lead means 24c extends a substantial distance from the back electrode and is conductively attached to the ground or reference electrode 11. The reference electrode is preferably mounted on a limb of an infant to provide a stronger ECG signal and the lead 24c is accordingly arranged to extend a distance, for example about six or eight inches, from the back electrode to enable mounting of the reference electrode on a limb of the infant when the back electrode is mounted on the infant's back. The multi-conductor cable 24 is conveniently of a four conductor type which can be used with a conventional four terminal RJ11 connector 28, and it is preferable to extend two of the conductors 24c to the reference electrode 11, to provide greater strength In order to facilitate assembly of the leads on the electrode members, the leads are preferably formed as a sub-assembly with the leads 24a and 24b cut to an appropriate length and the ends stripped and pieces 31 of pressure sensitive tape applied to the stripped ends as shown in FIGS. 4 and 8. The tape 31 is then used to press the unsheathed ends of the leads on to the respective electrodes 17 and 18. The piece of double sided pressure sensitive tape 31 is preferably applied to the electrodes and to the ends of the leads in a manner such that the stripped ends of each lead are sandwiched between two portions of the conductive pressure sensitive tape. More specifically, the lower face of one portion of the tape is directly adhered to the upper face of the electrode and the stripped end of the lead and a portion of the sheathing overlies and is embedded in the pressure sensitive adhesive on the upper face of portion. A second portion of the tape overlies and is adhered to the stripped end of the lead and the first mentioned tape portion. This can conveniently be achieved by folding a piece of the double sided pressure sensitive tape around the end of each lead to form a tape flag as shown in FIG. 8 and thereafter pressing the tape flag onto the electrode. If the double sided pressure sensitive tape has release liners on both sides, one release liner is removed prior to folding and the other release liner is removed during or after folding. Sandwiching the carbon filaments between two layers of the conductive pressure sensitive tape substantially improves conductivity between the lead and the electrode over that obtained when a one layer of tape is used.

Figure 2:
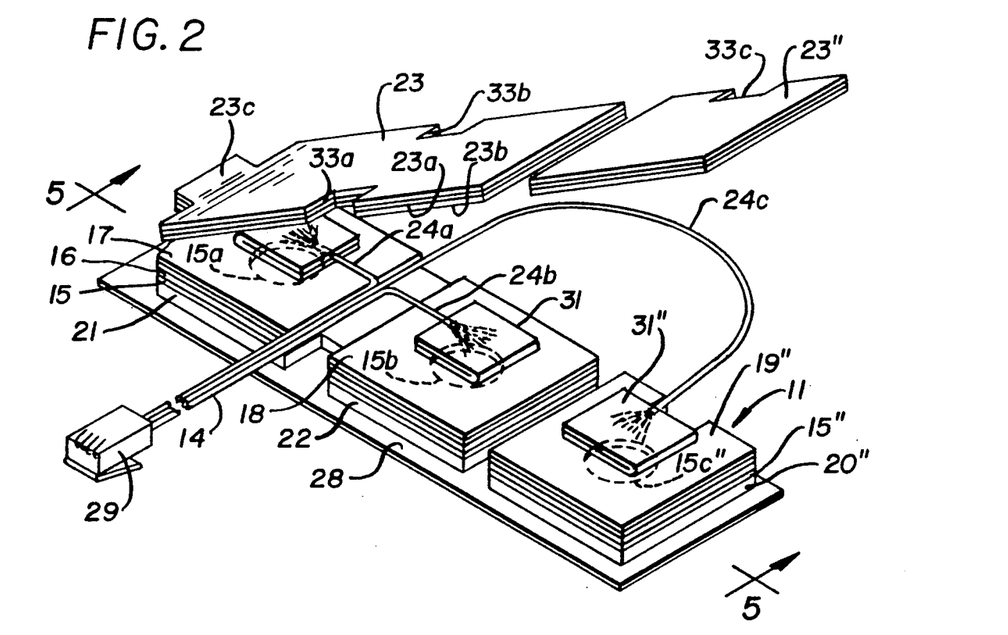
FIG. 2 is a perspective view of one embodiment of the electrode assembly with the thickness of the parts exaggerated to facilitate illustration.
Figure 3:
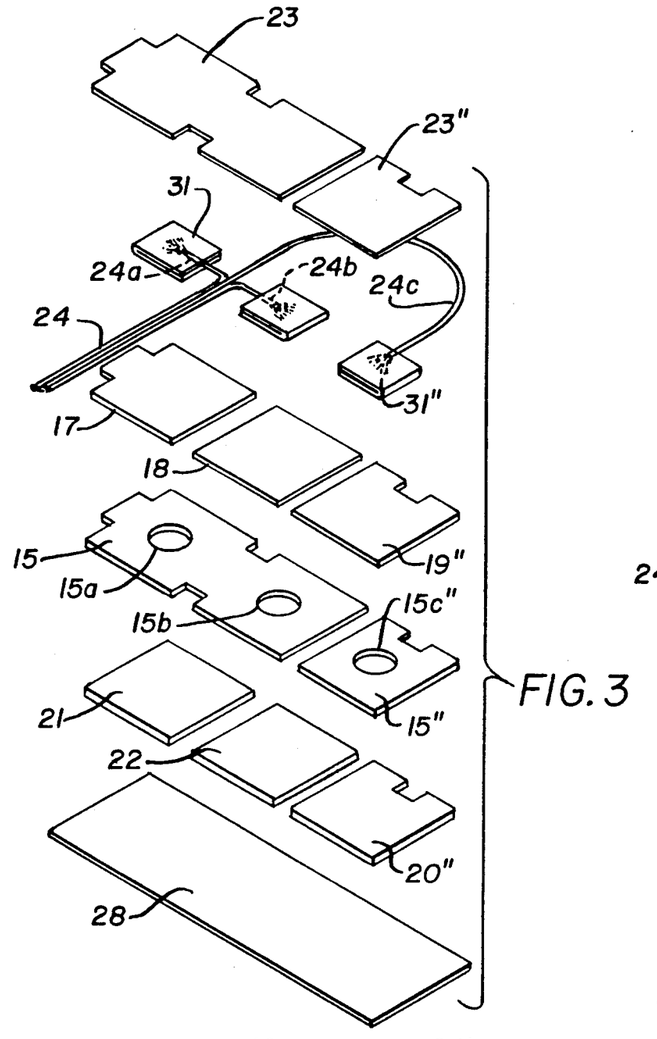
FIG. 3 is an exploded perspective view of the back electrode assembly with the thickness of the parts exaggerated to facilitate illustration.
Figure 5:
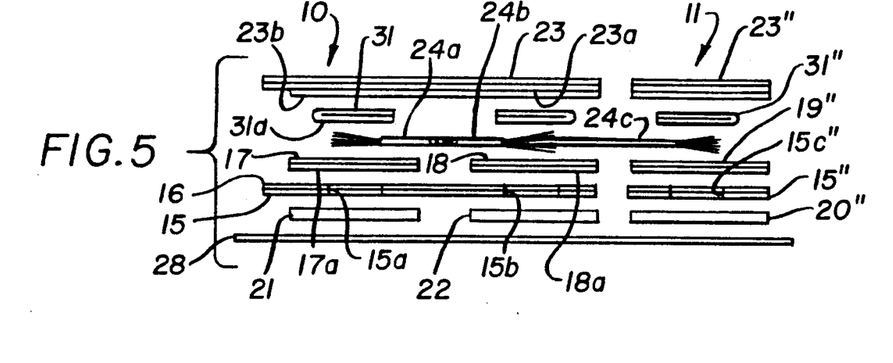
FIG. 5 is a stylistic exploded sectional view taken on the plane 5—5 of FIG. 2, with the thickness of the parts exaggerated to facilitate illustration.

The X-ray transparent cover member 23 of electrically insulative material, is provided to cover the electrodes and to aid in anchoring the conductors to the back electrode. The cover member may, for example, be formed from a soft non-woven spun laced fabric of polyester such as sold by E. I. Dupont under the trademark Sontara or a thin soft layer of foamed plastic such as polyurethane foam. The cover member 23 is preferably provided with a layer of pressure sensitive adhesive 23a at its under side adapted to adhesively attach the cover member to the back electrode. The cover member can be precut to a suitable size and shape. However, in order to facilitate trimming of the cover member at the same time the other components of the back electrode are trimmed, only a portion 23c of the cover sheet is secured to the web member as shown in FIG. 5, with a release sheet 23b underlying the remainder of the adhesive coating on the cover member. After the cover member has been trimmed together with the electrode members, the cover member can be raised as shown in FIG. 2 and the lead wire sub-assembly can be then mounted on the electrodes 17 and 18. The release sheet is then peeled off to allow the remainder cover member to be pressed onto the electrode members and adhesively secured thereto by the adhesive coating 23a.

The reference electrode 11, when mounted on the limb of the infant, is generally outside the chest area to be X-rayed and it is not essential that the reference electrode have an X-ray translucent construction and various known single electrode type electrode constructions can be used. For example, the reference electrode 11 can be of the type disclosed in the applicant's prior U.S. Pat. No. 4,911,169 and used with or without a limb band.

In the embodiment illustrated, the reference electrode 11 is made with a layered construction substantially the same as that described above in connection with the back electrode 10 to provide an X-ray translucent reference electrode. The X-ray translucent multi-element back electrode and an X-ray translucent reference electrode can advantageously be formed in sets at the same time on a multi-station laminating machine.

A preferred method for making the electrode assembly to control spacing between the two electrodes in the back electrode assembly and proper registration of the several parts of each electrode is illustrated in the drawings. FIGS. 6A, 6B, 6C and 6D diagrammatically illustrate preparation of several composite webs prior to lamination and FIG. 7 diagrammatically illustrates laminating the several webs and trimming of the electrodes from the laminated assembly. In the pre-lamination step illustrated in 6A, a first composite web 50 is provided comprising a layer of skin compatible hydrogel adhesive 51, a carrier release liner 52 at one side, and a second release liner 53 at the other side. The hydrogel adhesive is commonly provided with a mesh type support scrim, and this support scrim is preferably located relatively farther from release liner 52 than liner 53. Two slits 54 parallel to the length of the web at locations correlative with the desired interelectrode spacing, are formed in the web 50 as by rotary cutting blades (not shown), with the slits extending through the release liner 53 and through the hydrogel 51 but not through the release liner 51. The release liner 53 and the portion of the hydrogel layer between the slits 54 are stripped and removed from the web 50 before depositing at a laminating station A as shown in FIG. 7.

Figure 6A:
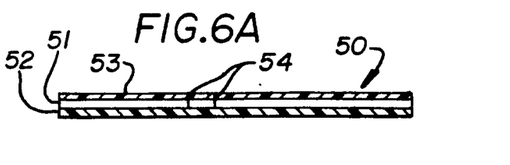
FIGS. 6A, 6B, 6C and 6D are diagrammatic views illustrating preparation of various laminations for assembly and production of the electrode assembly.
Figure 6B:
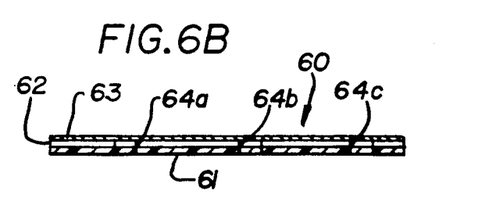
Figure 7:
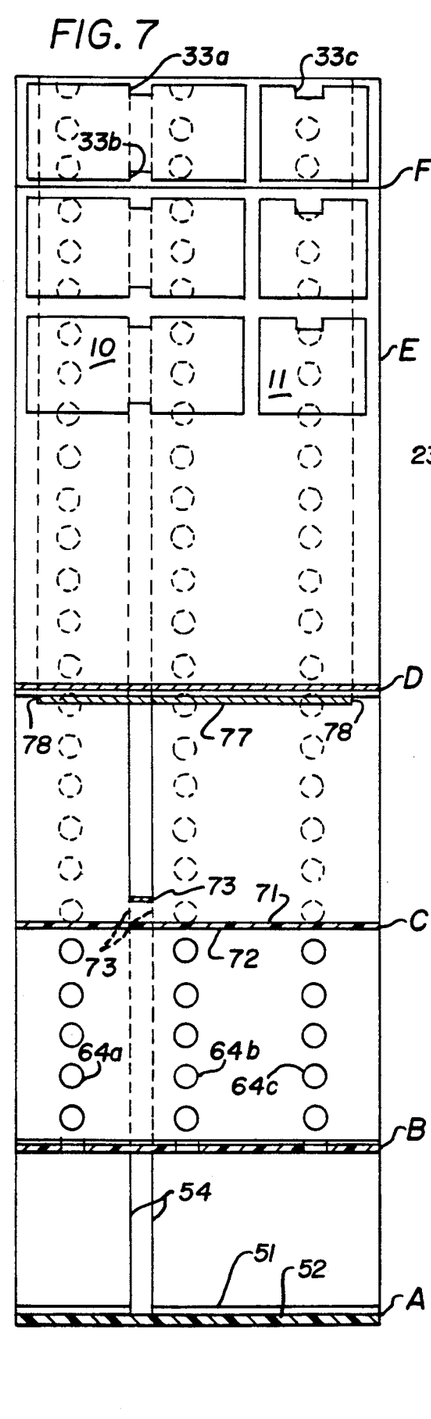
FIG. 7 is a diagrammatic view illustrating a method for assembling and producing a preferred embodiment of the electrode assembly.

As illustrated in FIG. 6B, a second composite web 60 is provided comprising a strip 61 of non-conductive paper or plastic with a layer 62 of adhesive on one side and a release liner 63 overlying the adhesive. Opening means 64a, 64b and 64c are provided in the web 60 at locations spaced apart crosswise of the web to correlate with the three electrodes being formed. The opening means may be provided by punching completely through the web or by punching from the side of the web opposite the release liner 63 and only partially or incompletely punched through the release liner so that the release liner 63 will aid in removing the punched holes when the release liner is stripped from the web prior to depositing the web at lamination station B as shown in FIG. 7. In order to avoid possible problems with registration of the openings with the electrodes at the subsequent trimming station, the openings may be sized and spaced apart in a direction lengthwise the web 61 in relation to the size of the electrodes such that one opening and at least portions of another opening or openings register with each electrode. Although the opening means 64a, 64b and 64c are illustrated as a plurality of punched openings spaced apart in a direction longitudinally of the web, it is also contemplated that the opening means could be continuous in a direction longitudinally of the web. For example, the web could be perforated longitudinally of the web in a manner to enable tearing or stripping out portions of the web along bands correlative with the lengthwise rows of openings 64a, 64b and 64c, prior to or during laminating of the web 60 to the layer of skin compatible adhesive.

Figure 6C:
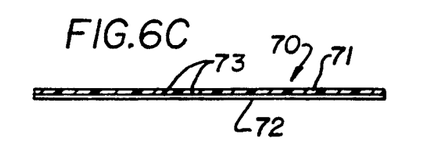

As shown at 6C, a third web 70 is provided comprising a strip of thin conductive carbon filled polmer 71 having a silver-silver chloride coating 72 at one side. Two rows of micro perforations 73 are formed in the web 70 at locations spaced from an edge of the web 71 correlative with the spacing of the slits 54 in the web 53, and the portion 73a of the strip between the perforations 73 is stripped from the web 71 and removed just prior to or during depositing of the web at lamination station C in FIG. 7.

Figure 6D:
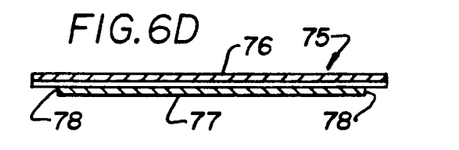

As shown in FIG. 6D, a fourth composite web 75 is provided and comprises a cover member 76 of soft electrically insulative material, a layer 77 of adhesive on the underside of the member 76, and a release liner 77 underlying the adhesive layer. The release liner 77 is a double sided release liner and is trimmed, either before or after lamination to the cover member, to a width narrower than the cover member 76, and such that opposite side edges 78 of the release liner are spaced inwardly of the side edges of the cover member to expose portions of the adhesive layer 77 along opposite sides of the cover member. With this arrangement the cover member 76 will adhere to web 70 only opposite side edges when it is laminated at station D to the web.

Thereafter, the several layers are cut-out or trimmed against the release strip 52 at station E to form the back electrode 10 and reference electrode 11 and the release strip 52 is subsequently cut through as indicated by line F in FIG. 7. The release strip is preferably cut at F so that one back electrode and one reference electrode remain connected as a set by the cut-off portion of the release sheet 52, to facilitate subsequent assembly of the leads on the electrodes and handling of the electrode after assembly. The trim die is preferably arranged to form notches 33a and 33b in the back electrode at the locations at which the lead means 24 enters and exits from the back electrode 10 and also form a notch 33c where the lead means 24c enters the reference electrode 11 so that a pull or force on the lead means in a direction transverse to the plane of the electrodes will be transmitted to the electrodes at a location inwardly of the margin of the electrodes reduce the likelihood of peeling the electrode off the skin of the patient.

The reference electrode formed in the manner described above, has the same layered construction as the back electode. More specifically, the reference electrode includes a patch 20" of hydrogel adhesive, a web 15" of non-conductive material having an opening 15c" therethrough, an X-ray translucent electrode member 19" of carbon filled polymer material, and a cover member 23" of X-ray translucent electrically insulative material.

After triming and severing, the cover member 23 on the back electrode is raised or lifted and the leads 24a and 24b affixed to the upper face of the electrode members 17 and 18 with a piece of pressure sensitive adhesive tape 30 as previously described. After removal of the release liner, the cover member 23 is reapplied to the back electrode. Similarly, the cover member 23" on the reference electrode 11" is raised and the distal end of leads 24c affixed as by a piece of tape 31" to the upper face of the reference electrode member 19" in the manner previously described in connection with leads 24a and 24b, and the cover member 23" reapplied after removal of the release liner.

The embodiments of the invention in which an exclusive property or privilege is claimed are defined as follows:

1. A monitoring electrode comprising: at least one X-ray transparent sheet electrode member of thin flexible material having upper and lower faces and a thin silver/silver chloride coating on the lower faces, a web member of thin flexible X-ray transparent electrically insulative material having upper and lower faces, the web member having an adhesive coating on the upper face adhered to the lower face of the sheet electrode member, the web member covering only one portion of the lower face of the electrode member, a patch of skin compatible conductive adhesive on a portion of the lower face of the web member and directly contacting a second portion of the lower face of the sheet electrode member, removable carrier sheet means on a lower side of the patch of skin compatible conductive adhesive for covering the latter prior to use, an X-ray transparent electrical lead including a carbon fiber conductor sheathed in an X-ray transparent insulating material, the lead having an unsheathed portion with exposed carbon fibers at one end, X-ray transparent attaching means conductively attaching the carbon fiber conductor at said one end to the upper face of the sheet electrode member, and a cover member of X-ray transparent electrically insulative material having a pressure sensitive adhesive on a lower face thereof adhesively attaching the cover member to the upper face of the sheet electrode member and adhesively engaging the lead adjacent said one end of the lead.

2. A monitoring electrode according to claim 1 wherein said web member has a portion extending outwardly of the periphery of the sheet electrode member and adhered by the adhesive coating on the upper face thereof to the lead adjacent said one end of the lead.

3. A monitoring electrode according to claim 1 wherein said attaching means comprises an electrically conductive X-ray transparent coating on the carbon fibers and means for holding the coated fibers in contact with said upper face of the sheet electrode member.

4. A monitoring electrode according to claim 3 wherein the electrically conductive X-ray transparent coating comprises an ink impregnated with electrically conductive particles.

5. A monitoring electrode according to claim 1 wherein the lead extends from one edge of the monitoring electrode and said cover member has a notch in said one edge thereof at a location where the lead extends from the electrode.

6. A monitoring electrode according to claim 1 wherein said attaching means comprises a piece of double sided pressure sensitive tape having electrical conductivity in the plane of the tape and transverse to the plane of the tape.

7. A monitoring electrode according to claim 1 wherein said attaching means comprises a piece of tape having a conductive fiber matte and a conductive pressure sensitive adhesive coating on opposite sides of the matte, the tape having electrical conductivity in the plane of the tape and transverse to the plane of the tape, the tape being adhered to the upper face of the electrode member and to the carbon fibers at said one end of the lead.

8. A monitoring electrode comprising: at least one X-ray transparent sheet electrode member of thin flexible material having upper and lower faces and a thin silver/silver chloride coating on one of the faces, a patch of skin compatible conductive adhesive contacting at least a portion of the lower face of the sheet electrode member, removable carrier sheet means on a lower side of the patch of conductive adhesive for covering the latter prior to use, an X-ray transparent electrical lead including a carbon fiber conductor sheathed in an X-ray transparent insulating material, the lead having an unsheathed portion with exposed carbon fibers at one end, X-ray transparent attaching means conductively attaching the carbon fiber conductor at said one end of the lead to the upper face of the sheet electrode member, and a cover member of X-ray transparent electrically insulative material having a pressure sensitive adhesive on a lower face thereof adhesively attaching the cover member to the upper face of the sheet electrode member and adhesively engaging the lead adjacent said one end of the lead, said attaching means comprising a piece of double sided pressure sensitive tape having electrical conductivity in the plane of the tape and transverse to the plane of the tape, the tape being adhered to the upper face of the electrode member and to the exposed carbon fibers at said one end of the lead.

9. A monitoring electrode according to claim 8 wherein said attaching means comprises a piece of tape having a conductive fiber matte and a conductive pressure sensitive adhesive coating on opposite sides of the matte, the tape having electrical conductivity in the plane of the tape and transverse to the plane of the tape.

10. A monitoring electrode according to claim 9 wherein one portion of the tape is directly adhered to the upper face of the electrode member and to said one end of the lead at an underside of the latter, the tape having another portion overlying and adhered to said one portion of the tape and to said lead at a side opposite said underside.

11. A monitoring electrode assembly comprising:
   a) a multi-element back electrode including:
      i) X-ray transparent first and second sheet electrode members of thin flexible material each having upper and lower faces and a thin silver/silver chloride coating on one of the faces,
      ii) an X-ray transparent web member of thin electrically insulative material having upper and lower faces and an adhesive coating on the upper face, the web member having a first portion adhered to the lower face of the first sheet electrode member and a second portion adhered to the lower face of the second electrode member and a central portion intermediate the first and second electrode members, the web member covering only one portion of the lower face of the first sheet electrode member and covering only one portion of the lower face of the second sheet electrode member,
      iii) a first layer of skin compatible conductive adhesive on the lower face of the first portion of the web member and directly contacting a second portion of the lower face of the first sheet electrode member, a second layer of skin compatible conductive adhesive on the lower face of the second portion of the web member and directly contacting a second portion of the lower face of the second sheet electrode member;
   b) X-ray transparent first and second electrical leads each including a carbon fiber conductor sheathed in an electrically insulative material, the first and second electrical leads having electrical connector means at a first end thereof for making connection to a monitoring instrument, the first and second leads each having an intermediate section overlying the central portion of the web member and adhered to the adhesive coating on the upper face of the web member, first X-ray transparent attaching means conductively attaching the carbon fiber conductor at a second end of the first lead to the upper face of the first sheet electrode member, second X-ray transparent attaching means conductively attaching the carbon fiber conductor at a second end of the second lead to the upper face of the second sheet electrode member;
   c) a cover member of X-ray transparent electrically insulative material having an adhesive coating on a lower face thereof overlying and adhered to the upper faces of the first and second sheet electrode members; and
   d) removable carrier sheet means on a lower side of the first and second layers of skin compatible conductive adhesive for covering the latter prior to use.

12. A monitoring electrode assembly according to claim 11 wherein said first and second X-ray transparent attaching means each include an electrically conductive coating on the carbon fibers and means for holding the coated fibers in contact with the upper face of the respective first and second electrode members.

13. A monitoring electrode according to claim 11 wherein each of said attaching means comprises a piece of tape having a conductive fiber matte and a conductive pressure sensitive adhesive coating on opposite sides of the matte, the tape having electrical conductivity in the plane of the tape and transverse to that plane.

14. A monitoring electrode assembly comprising:
   a) a multi-element back electrode including:
      i) an X-ray transparent cover member of thin flexible electrically insulative material having upper and lower faces, the cover member having first and second electrode zones and a central zone intermediate the first and second electrode zone;
      ii) X-ray transparent first and second sheet electrode members of thin flexible material each having upper and lower faces and a thin silver/silver chloride coating on one of the faces, the first and second electrode members being adhesively attached to the cover member respectively in said first and second electrode zones;
      iii) first and second layers of skin compatible conductive adhesive respectively contacting at least a portion of the lower face of the first and second sheet electrode members;
   b) a reference electrode adapted for positioning remote from the back electrode, the reference electrode including:
      i) a reference electrode member,
      ii) a third layer of skin compatible conductive adhesive contacting a lower side of the reference electrode member;
   c) X-ray transparent first, second and third electrical leads each including a carbon fiber conductor sheathed in an electrically insulative material, the first, second and third leads having electrical connector means on a first end thereof for making connection to an instrument and a first lead section extending from the connector means to the central zone of the cover member, the first, second and third leads having an intermediate section adhesively attached to the cover member, first X-ray transparent attaching means conductively attaching the carbon fiber conductor at a second end of the first lead to the first sheet electrode member, second X-ray transparent attaching means conductively attaching the carbon fiber conductor at a second end of the second lead to the second sheet electrode member, the third lead having a length substantially longer than the first and second leads to extend a substantial distance beyond the back electrode, and third means conductively attaching the carbon fiber conductor at a second end of the third lead to the reference electrode member; and d) removable release sheet means on a lower side of each of the first, second and third layers of skin compatible conductive adhesive for covering the latter prior to use.

15. A monitoring electrode according to claim 14 wherein each of said attaching means comprises a piece of tape having a conductive fiber matte and a conductive pressure sensitive adhesive coating on opposite sides of the matte, the tape having electrical conductivity in the plane of the tape and transverse to that plane.

16. A monitoring electrode assembly comprising:
a) a multi-element back plate electrode including:
 i) x-ray translucent flexible first and second sheet electrode members of thin material each having an upper face and a lower face and a thin silver/silver chloride coating on one of the faces,
 ii) an x-ray transparent web member of thin flexible electrically insulative material having upper and lower faces and an adhesive coating on the upper face, the web member having a first portion adhered to the lower face of the first sheet electrode member and a second portion adhered to the lower face of the second sheet electrode member and a central portion intermediate the first and second electrode members, the web member covering only one portion of the lower face of the first sheet electrode member and covering only one portion of the lower face of the second sheet electrode member,
 iii) a first layer of skin compatible conductive adhesive on the lower face of the first portion of the web member and directly contacting a second portion of the lower face of the first sheet electrode member and a second layer of skin compatible conductive adhesive on the lower face of the second portion of the web member and directly contacting a second portion of the lower face of the second sheet electrode member;
b) a reference electrode adapted for positioning remote from the back electrode and including;
 i) a reference electrode member;
 ii) a third layer of skin compatible conductive adhesive on a lower side of the reference electrode member for connecting the reference electrode member to the skin of a patient;
c) x-ray transparent first and second and third electrical leads each including a carbon fiber conductor sheathed in an electrically insulative material, the first, second and third electrical leads having electrical connectors at a first end thereof and an intermediate section adhesively attached to the web member, first x-ray transparent attaching means conductively attaching the carbon fiber conductor at a second end of the first lead to the upper face of the first sheet electrode member, second x-ray transparent attaching means conductively attaching the carbon fiber conductor at a second end of the second lead to the upper face of the second sheet electrode member, the third lead having a length substantially longer than the first and second leads to extend a substantial distance from the back electrode, and means conductively attaching the carbon fiber conductor at a second end of the third lead to the reference electrode member;

d) an x-ray transparent cover member of electrically insulative material having an adhesive coating on a lower face thereof overlying and adhered to the upper faces of the first and second sheet electrode members and to said intermediate sections of the first, second and third leads, and e) removable carrier sheet means on a lower side of each of the first, second and third layers of skin compatible conductive adhesive for covering the latter prior to use.

17. A monitoring electrode assembly according to claim 16 wherein the back plate electrode has a pair of opposing long side edges and a pair of opposing short side edges, the central portion of the web member being substantially mid-way between the short side edges, the first, second and third leads extending from the central portion of the web member at one long side edge of the back plate electrode to the electrical connectors and the third lead extending from the central portion of the web member at the other long edge of the back plate electrode to the reference electrode.

18. A monitoring electrode assembly according to claim 17 including notches in the edges of the cover member at locations where the leads extend from the back plate electrode.

19. A monitoring electrode assembly according to claim 16 wherein said intermediate portions of said first, second and third leads are adhesively attached to the web member at said central portion.

20. A monitoring electrode assembly according to claim 16 wherein said first and second sheet electrode members are imperforate sheets of carbon filled polymer and each of said attaching means comprises an electrically conductive X-ray transparent coating on the carbon fibers.

21. A monitoring electrode assembly according to claim 16 wherein said first and second electrode members are fine mesh screens.

22. A monitoring electrode assembly according to claim 16 wherein the reference electrode comprises a X-ray transparent third sheet electrode member of thin flexible material having upper and lower faces, a second web member of thin flexible X-ray transparent electrically insulative material having upper and lower faces, the second web member having an adhesive coating on the upper face adhered to the lower face of the third sheet electrode member and covering only one portion of the lower face of the third sheet electrode member, and said third layer of skin compatible conductive adhesive on the lower face of the second web member directly contacting a second portion of the lower face of the third sheet electrode member.

23. A monitoring electrode according to claim 16 wherein each of said attaching means comprises a piece of tape having a conductive matte and a conductive pressure sensitive adhesive coating on opposite sides of the matte, the tape having electrical conductivity in the plane of the tape and transverse to the plane of the tape.

24. The method of forming an X-ray transparent monitoring electrode comprising:
   a) providing an X-ray transparent sheet electrode member of thin flexible material having upper and lower faces with a skin compatible adhesive contacting at least a portion of the lower face,
   b) providing an X-ray transparent electrical lead having a carbon fiber conductor sheathed in an X-ray transparent insulating material and with the sheath removed from one end of the lead; and
   c) adhesively attaching the carbon fiber conductor at said one end of the lead to the upper face of the electrode member with a piece of double sided pressure sensitive tape having a conductive graphite fiber matte and a conductive pressure sensitive adhesive on opposite sides of the matte providing conductivity in the plane of the tape and transverse to the plane of the tape.

25. The method of claim 24 including applying the tape so that one portion of the tape is directly adhered to the upper face of the electrode member and is adhered to said one end of the lead at an underside of the latter and another portion of the tape is adhered to said one portion of the tape and to said lead at a side opposite said underside.

26. An X-ray transparent monitoring electrode comprising, an X-ray transparent sheet electrode member of thin flexible material having upper and lower faces, a skin compatible conductive adhesive contacting at least a portion of the lower face of the sheet electrode member, an X-ray transparent electrical lead having a carbon fiber conductor sheathed in an X-ray transparent insulating material, the lead having an unsheathed portion with exposed carbon fiber conductors at one end, and a piece of double sided pressure sensitive tape having a conductive graphite fiber matte and a conductive pressure sensitive adhesive on opposite sides of the matte providing electrical conductivity in the plane of the tape and transverse to the plane of the tape, the tape being adhered to the upper face of the electrode member and to the exposed carbon fibers at said one end of the lead.

27. A monitoring electrode according to claim 26 wherein one portion of the tape is directly adhered to the upper face of the electrode member and to said one end of the lead at an underside of the latter, the tape having another portion overlying and adhered to said one portion of the tape and to said lead at a side opposite said underside.

* * * * *